United States Patent
Jeon et al.

(10) Patent No.: US 10,434,967 B2
(45) Date of Patent: Oct. 8, 2019

(54) TROUBLE SHOOTING APPARATUS AND METHOD FOR BIO-SIGNAL SENSOR EQUIPPED IN VEHICLE

(71) Applicants: Hyundai Motor Company, Seoul (KR); OMRON AUTOMOTIVE ELECTRONIC KOREA CO., LTD., Anseong-si (KR)

(72) Inventors: Seul Ki Jeon, Suwon-si (KR); Nam Woong Hur, Hwaseong-si (KR); Eung Hwan Kim, Seoul (KR); Shinichi Kuroyanagi, Komaki (JP); Taek Soo Han, Uiwang-si (KR)

(73) Assignees: Hyundai Motor Company, Seoul (KR); OMRON AUTOMOTIVE ELECTRONIC KOREA CO., LTD., Anseong-si (KR)

( * ) Notice: Subject to any disclaimer, the term of this patent is extended or adjusted under 35 U.S.C. 154(b) by 408 days.

(21) Appl. No.: 15/379,241

(22) Filed: Dec. 14, 2016

(65) Prior Publication Data
US 2017/0313274 A1   Nov. 2, 2017

(30) Foreign Application Priority Data

Apr. 28, 2016  (KR) .................. 10-2016-0052015

(51) Int. Cl.
| | |
|---|---|
| *G06F 11/30* | (2006.01) |
| *B60R 21/015* | (2006.01) |
| *A61B 5/00* | (2006.01) |
| *A61B 8/02* | (2006.01) |
| *A61B 8/08* | (2006.01) |
| *B60W 40/08* | (2012.01) |

(Continued)

(52) U.S. Cl.
CPC ........ *B60R 21/01542* (2014.10); *A61B 5/024* (2013.01); *A61B 5/6893* (2013.01); *A61B 5/7207* (2013.01); *A61B 8/02* (2013.01); *A61B 8/488* (2013.01); *A61B 8/5269* (2013.01); *B60R 21/015* (2013.01); *B60W 40/08* (2013.01); *A61B 5/021* (2013.01); *A61B 5/02444* (2013.01); *A61B 5/0507* (2013.01); *A61B 2503/22* (2013.01); *A61B 2560/0276* (2013.01); *B60W 2040/0881* (2013.01)

(58) Field of Classification Search
CPC .............................................. B60R 21/01542
See application file for complete search history.

(56) References Cited

U.S. PATENT DOCUMENTS

2014/0288762 A1* 9/2014 Sakayori ............... F02D 41/123
                                                             701/31.3

FOREIGN PATENT DOCUMENTS

| JP | 2003-118421 | 4/2003 |
| JP | 2007-331490 A | 12/2007 |

(Continued)

*Primary Examiner* — Phuong Huynh
(74) *Attorney, Agent, or Firm* — Morgan, Lewis & Bockius LLP (57) ABSTRACT

A fault diagnosis method for a bio-signal sensor for the vehicle includes measuring a first bio-signal through the bio-signal sensor in response to a seating detecting signal, measuring a second bio-signal through the bio-signal sensor in response to input through an on-board interface, and determining whether the bio-signal sensor may have malfunctioned according to whether the second bio-signal includes a signal deviating from a range set in response to the first bio-signal.

20 Claims, 6 Drawing Sheets

(51) Int. Cl.
*A61B 5/024* (2006.01)
*A61B 5/021* (2006.01)
*A61B 5/05* (2006.01)

(56) References Cited

FOREIGN PATENT DOCUMENTS

| | | |
|---|---|---|
| JP | 2008-13053 A | 1/2008 |
| JP | 2009-25533 A | 2/2009 |
| JP | 2010-265757 A | 11/2010 |
| KR | 10-2007-0059206 A | 6/2007 |
| KR | 10-1318854 B1 | 10/2013 |
| KR | 10-2014-0022312 | 2/2014 |
| KR | 10-2015-0009729 | 1/2015 |

\* cited by examiner

TROUBLE SHOOTING APPARATUS AND METHOD FOR BIO-SIGNAL SENSOR EQUIPPED IN VEHICLE

The present application claims priority to Korean Patent Application No. 10-2016-0052015, filed on Apr. 28, 2016 in the Korean Intellectual Property Office, the entire contents of which is incorporated herein for all purposes by this reference.

BACKGROUND OF THE INVENTION

Field of the Invention

The present invention relates to trouble shooting method and apparatus for a bio-signal sensor in a vehicle and, more specifically, to a method and apparatus for determining whether a sensor for detecting driver's or user's bio-signal, operates properly, in order to improve operation reliability.

Discussion of the Related art

Vehicles have been developed to provide more convenient and safer driving environments to drivers. For example, when a driver dozes off due to long distance driving, tiredness or boredom during highway driving, accidents may occur, leading to loss of life and material loss. Accordingly, drivers drive cars while checking surrounding situations such as rear traffic conditions in order to change lanes or turn left or right while securing a front field of vision of a predetermined distance or longer all the time, and thus the drivers may feel weary and doze off. Therefore, there have been proposed methods and apparatuses for preventing a driver who is driving a car from dozing off by sensing a pulse rate of the driver during driving, comparing the sensed pulse rate with an average pulse rate of the driver, detecting a difference between the sensed pulse rate and the average pulse rate and transmitting a warning sound according to a detected signal.

Meanwhile, there is growing interest in technologies for checking health in real time as interest in health and physical conditions increases. To check health in real time, bio-signals may be used. Bio-signal processing technology is developed as interface technology according to bio-signal processing or monitoring technology using bio-signals. The bio-signal interface technology refers to technology for extracting bio-signals and generating commands for controlling operations of medical apparatuses using the extracted bio-signals. The monitoring technology using bio-signals refers to technology of extracting characteristics of bio-signals to determine a disease or psychological state. Recently, technology for measuring the blood pressure of a driver using a steering wheel of a vehicle has been proposed, and thus a person who drives a car every day can measure and manage the blood pressure every day simply by gripping the steering wheel of the car.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an apparatus and method for delivering a detecting result with high reliability to a driver or a user through a method of diagnosing a failure in a bio-signal sensor mounted in a vehicle.

Various aspects of the present invention are directed to providing an apparatus and method for determining whether a bio-signal sensor mounted in a vehicle has malfunctioned while a driver or a user drives the vehicle and preventing the driver or user from being distracted while driving when the bio-signal sensor malfunctions, thereby promoting safe driving.

It will be appreciated by persons skilled in the art that the objects that could be achieved with the present invention are not limited to what has been particularly described hereinabove and the above and other objects that the present invention could achieve will be more clearly understood from the following detailed description.

In an aspect of the present invention to accomplish the object, a fault diagnosis method for a bio-signal sensor for a vehicle includes: measuring a first bio-signal through the bio-signal sensor in response to a seating detecting signal; measuring a second bio-signal through the bio-signal sensor in response to input through an on-board interface; and determining whether the bio-signal sensor has malfunctioned according to whether the second bio-signal includes a signal deviating from a range set in response to the first bio-signal.

The fault diagnosis method may further include: measuring a third bio-signal when the engine of the vehicle is started; and determining whether the bio-signal sensor has malfunctioned according to whether the third bio-signal includes a signal deviating from the range set in response to the first bio-signal.

The input through the on-board interface may include at least one of variation in a steering wheel, variation in a pedal and variation in a shifter.

The input through the on-board interface may be generated after the engine of the vehicle is started.

The bio-signal sensor may include a pulse sensor, and the first bio-signal and the second bio-signal may include pulse-detecting signals.

The pulse sensor may be a non-contact Doppler pulse sensor.

The signal deviating from the range may include noise according to the input through the on-board interface.

The determining of whether the bio-signal sensor has malfunctioned may include: analyzing at least one of the second bio-signal and the third bio-signal to output a result within the range; determining whether the signal deviating from the range corresponds to the input through the on-board interface; and determining whether the bio-signal sensor has malfunctioned in response to the determination result.

The fault diagnosis method may further include stopping operation of the bio-signal sensor when the bio-signal sensor is determined to have malfunctioned.

In another aspect of the present invention, an apparatus is for performing a fault diagnosis of a bio-signal sensor in a vehicle including a processing system that includes at least one data processor and at least one computer-readable memory storing a computer program. Herein, the processing system is configured to cause the apparatus to: measure a first bio-signal through the bio-signal sensor in response to a seating detecting signal; measure a second bio-signal through the bio-signal sensor in response to input through an on-board interface; and determine whether the bio-signal sensor has malfunctioned according to whether the second bio-signal includes a signal deviating from a range set in response to the first bio-signal.

In another aspect of the present invention, a non-transitory computer readable medium can store a program causing a processing system to execute a process for performing a fault diagnosis of a bio-signal sensor in a vehicle. The process includes measuring a first bio-signal through the bio-signal sensor in response to a seating detecting signal; measuring a second bio-signal through the bio-signal sensor in response to input through an on-board interface; and determining whether the bio-signal sensor has malfunctioned according to whether the second bio-signal includes a signal deviating from a range set in response to the first bio-signal.

In another aspect of the present invention, a fault diagnosis apparatus for a bio-signal sensor for a vehicle includes: a receiver for receiving a first bio-signal measured through the bio-signal sensor in response to a seating detecting signal and a second bio-signal measured through the bio-signal sensor in response to input through an on-board interface; and a determination unit for determining whether the bio-signal sensor has malfunctioned according to whether the second bio-signal includes a signal deviating from a range set in response to the first bio-signal.

The receiver may receive a third bio-signal when the engine of the vehicle is started, and the determination unit may determine whether the bio-signal sensor has malfunctioned according to whether the third bio-signal includes a signal deviating from the range set in response to the first bio-signal.

The fault diagnosis apparatus may further include an external signal input device for receiving input through the on-board interface.

An external signal input to the external signal input device may be generated by at least one of variation in a steering wheel, variation in a pedal and variation in a shifter.

The external signal may be generated after the engine of the vehicle is started.

The bio-signal sensor may include a pulse sensor, and the first bio-signal and the second bio-signal may include pulse-detecting signals.

The pulse sensor may be a non-contact Doppler pulse sensor.

The signal deviating from the range may include noise according to the input through the on-board interface.

The fault diagnosis apparatus may further include an operation unit for analyzing at least one of the second bio-signal and the third bio-signal to output a result within the range.

The determination unit may determine whether the signal deviating from the range corresponds to the input through the on-board interface and determine whether the bio-signal sensor has malfunctioned in response to the determination result.

The fault diagnosis apparatus may further include a controller for stopping operation of the bio-signal sensor when the bio-signal sensor is determined to have malfunctioned.

The controller may control operation of the bio-signal sensor to cause the bio-signal sensor to periodically measure a bio-signal and to output measured bio-signals to the receiver.

The aforementioned aspects of the present invention are merely parts of preferred embodiments of the present invention and various embodiments reflecting the technical features of the present invention can be derived and understood by those skilled in the art on a basis of the detailed description which will be given below.

A description will be given of the advantages of the apparatus according to an exemplary embodiment of the present invention.

The present invention can rapidly check whether a bio-signal sensor capable of detecting the pulse of a user or a driver in a non-contact manner has malfunctioned.

In addition, the present invention can check a failure in the bio-signal sensor mounted in a vehicle to prevent misdiagnosis of health of a user or a driver and disturbing driving when wrong information is delivered to the user or driver.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

The present invention will now be described in more detail through preferred embodiments with reference to the accompanying drawings. The terms "module", "unit" or "part" used to signify components are used herein to aid in understanding of the components and thus they should not be considered as having specific meanings or roles.

In the following description of the embodiments, it will be understood that, when an element is referred to as being "on" or "under" another element, it can be "directly" on or under another element or can be "indirectly" formed such that an intervening element is also present. Furthermore, the expression "on" or "under" may be used herein to represent the relationship of one element to another element as illustrated in the figures. It will be understood that this expression is intended to encompass different orientations of the elements in addition to the orientation depicted in the figures, namely, to encompass both "on" and "under".

Figure 1:
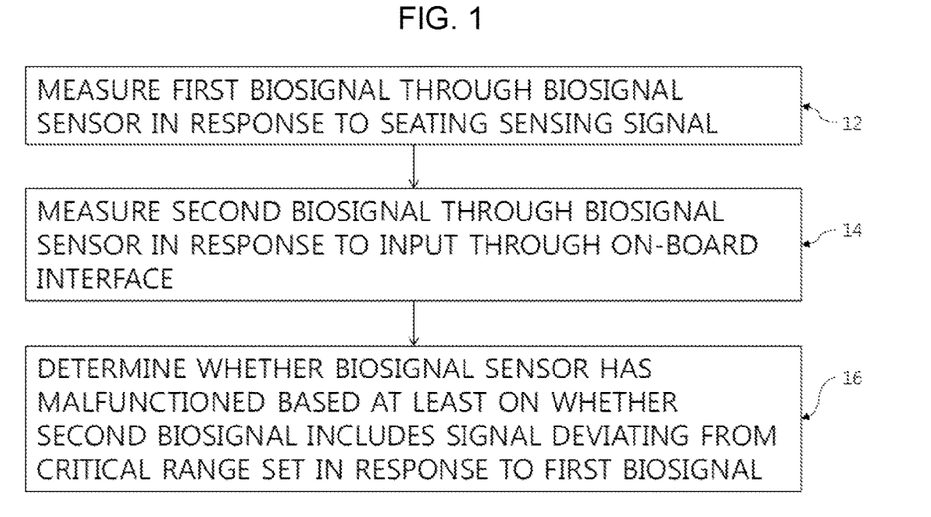
FIG. 1 illustrates a method of diagnosing a fault of a bio-signal sensor for vehicles.

FIG. 1 illustrates a method of diagnosing a fault of a bio-signal sensor for vehicles.

As shown, the method of diagnosing a fault of the bio-signal sensor for a vehicle may include a step 12 of measuring a first bio-signal through the bio-signal sensor in response to a seating detecting signal, a step 14 of measuring a second bio-signal through the bio-signal sensor in response to input through an on-board interface, and a step 16 of determining whether the bio-signal sensor has malfunctioned according to whether the second bio-signal includes a signal deviating from a range set corresponding to the first bio-signal.

The bio-signal sensor may measure a bio-signal of a user or a driver of the vehicle through a predetermined method. The user or driver who is driving the vehicle or gets in the vehicle moves bodily to manipulate the on-board interface. User's or driver's motion can generate noise. The bio-signal sensor may receive noise as well as bio-signals. When the bio-signal sensor receives noise caused by a specific motion of the user or driver, the bio-signal sensor may be determined to normally operate. When the bio-signal sensor does not receive noise caused by a specific motion of the user or driver, it is difficult to determine that the bio-signal sensor normally operates. Accordingly, it is possible to diagnose a fault of the bio-signal sensor according to whether the bio-signal sensor can receive noise corresponding to a specific motion of the user or driver.

The first bio-signal may be measured in response to the seating detecting signal. The seating detecting signal may be generated by a seating sensor configured for detecting a state in which the user or driver sits on a seat. When the user or driver sits on a seat, the bio-signal sensor may measure the first bio-signal. The environment of the user or driver when the first bio-signal is measured may have relatively low noise. The first bio-signal measured in this situation may be used to set the range.

The input through the on-board interface may include at least one of variation in a steering wheel, variation in a pedal and variation in a shifter. A motion of the user or driver may be generated at any time. However, when the input through the on-board interface is generated, the vehicle may easily recognize the motion of the user or driver. When the user or driver manipulates the steering wheel, acceleration pedal, brake pedal or shifter, the user or driver generates a motion for manipulation and the vehicle may sense input corresponding to manipulation of the user or driver.

The input through the on-board interface may be applied after the engine of the vehicle is started. According to an embodiment, interface manipulation of the user or driver may be detected while electric devices of the vehicle operate.

Although not shown in the figure, the method of diagnosing a fault of the bio-signal sensor may further include a step of measuring a third bio-signal when the engine of the car is started and a step of determining whether the bio-signal sensor has malfunctioned according to whether the third bio-signal includes a signal deviating from the range set corresponding to the first bio-signal. When the engine of the car is started, noise including vibration may be generated. It is possible to diagnose a fault of the bio-signal sensor through the engine ignition of the vehicle instead of a motion of the user or driver.

In addition, the bio-signal sensor may include a pulse sensor and the first bio-signal and the second bio-signal may include pulse-detecting signals. The pulse sensor may be a non-contact Doppler pulse sensor. Various bio-signal sensors other than the Doppler pulse sensor may be mounted in the vehicle. A signal, which is received through the Doppler pulse sensor corresponding to a bio-signal sensor but does not belong to the range, may include noise according to input through the on-board interface. For example, the Doppler pulse sensor mounted in the vehicle transmits radio waves to the body of the driver and receives/analyzes a signal with respect to a Doppler variation in proportion to a pulse component to sense the pulse of the driver. This sensor may continuously output a wrong pulse value when the Doppler variation is not generated due to a failure in the transmission/reception function thereof.

The step 16 of determining whether the bio-signal sensor has malfunctioned may include a step of analyzing the second bio-signal and outputting a result within the critical range, a step of determining whether a signal deviating from the range corresponds to input through the on-board interface, and a step of deciding whether the bio-signal sensor has malfunctioned in response to the determination result, which are not shown in the figure. The third bio-signal may be used like the second bio-signal.

For example, the first bio-signal may be measured in an environment having low noise while the driver or user uses the car, and the second bio-signal and the third bio-signal may be received along with noise generated in response to a specific event including operation of the engine of the vehicle or interface manipulation by the user or driver. Accordingly, after the range of bio-signals is set using the first bio-signal, a fault of the bio-signal sensor may be diagnosed using the second or third bio-signal which may include noise deviating from the range.

The method of diagnosing a fault of the bio-signal sensor may further include a step of stopping operation of the bio-signal sensor upon determining that the bio-signal sensor has malfunctioned, after the step of determining whether the bio-signal sensor has malfunctioned. When it is determined that the bio-signal sensor does not normally operate, outputting no measurement result of the bio-signal sensor may be advantageous to the driver or user for safe driving because a measurement result of the bio-signal sensor may deliver incorrect information to the driver, causing misdiagnosis of health and disturbing normal driving. Furthermore, reliability may be improved by preventing the bio-signal sensor from delivering an incorrect measurement result to the driver or user.

Figure 2:
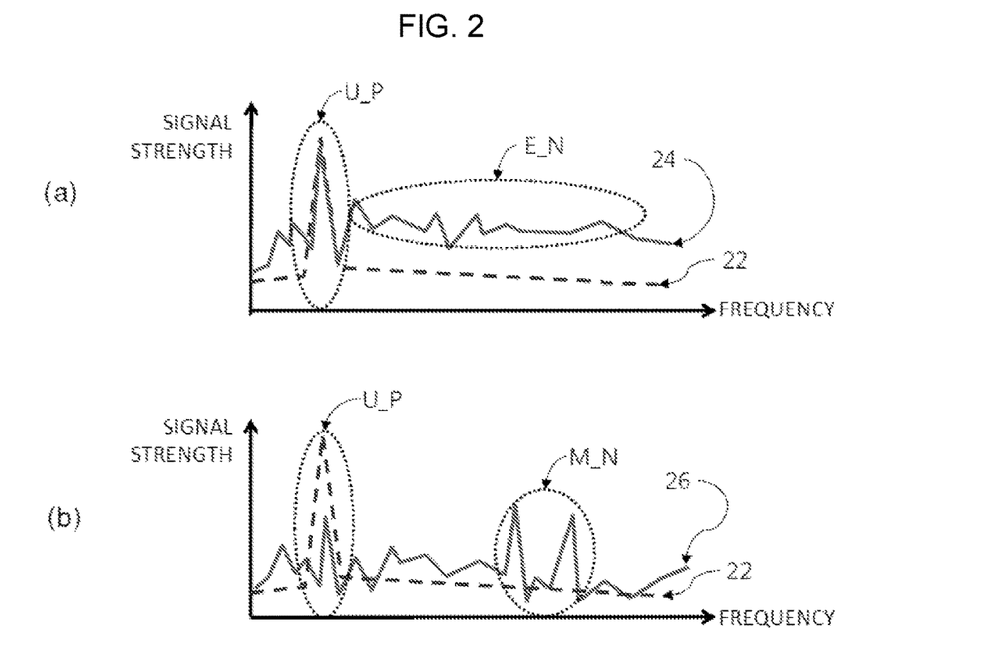
FIG. 2 illustrates signals detected by the bio-signal sensor for vehicles.

FIG. 2 illustrates signals detected by the bio-signal sensor for vehicles. Specifically, (a) illustrates signals detected by the bio-signal sensor when the engine of the vehicle is started and (b) illustrates signals detected by the bio-signal sensor when the user or driver manipulates the interface.

Referring to (a) in FIG. 2, the first bio-signal 22 measured in response to the seating detecting signal is compared with the third bio-signal 24 measured when the engine is started. Both the first bio-signal 22 and the third bio-signal 24 may include a measurement result U_P corresponding to the pulse of the user or driver. However, the first bio-signal 22 does not include particular noise at frequencies other than frequencies corresponding to the measurement result U_P, whereas the third bio-signal 24 includes noise E_N caused by vibration, noise and the like generated when the engine is started. Accordingly, it is possible to determine whether the bio-signal sensor mounted in the vehicle normally operates by checking whether the engine of the car is started and whether the third bio-signal 24 includes noise E_N which is not included in the first bio-signal 22.

While the case of (a) in FIG. 2 can be applied to a vehicle which generates vibration, noise and the like while the engine thereof is started, other methods may be necessary for vibration-free or noise-free vehicles since the vibration-free or noise-free vehicles do not generate noise even when the engines are started.

Referring to (b) in FIG. 2, the first bio-signal 22 measured in response to the seating detecting signal is compared with the second bio-signal 26 measured when the user manipulates the on-board interface. Both the first bio-signal 22 and the second bio-signal 26 may include a measurement result U_P corresponding to the pulse of the user or driver. However, the first bio-signal 22 does not include particular noise at frequencies other than frequencies corresponding to the measurement result U_P, whereas the second bio-signal 26 includes noise M_N caused by a motion of the user or driver. Accordingly, it is possible to determine whether the bio-signal sensor mounted in the vehicle normally operates by checking whether the second bio-signal 26 includes noise M_N which is not included in the first o-signal 22 in response to manipulation of the vehicle by the user or driver using the interface of the vehicle when the vehicle is driven.

For example, when the driver manipulates the pedal or steering wheel, noise may be generated due to physical movement. Particularly, such noise has characteristics that signal intensity (received signal strength) remarkably varies at a specific frequency although the variation may depend on movement of the driver. When the bio-signal sensor provided to the vehicle does not normally operate, such noise may not be sensed.

As described above, sensor reliability may be improved by applying a fault diagnosis function for radio signals to the bio-signal sensor in addition to the normal electrical fault diagnosis function of the bio-signal sensor (e.g., Doppler pulse sensor).

Figure 3:
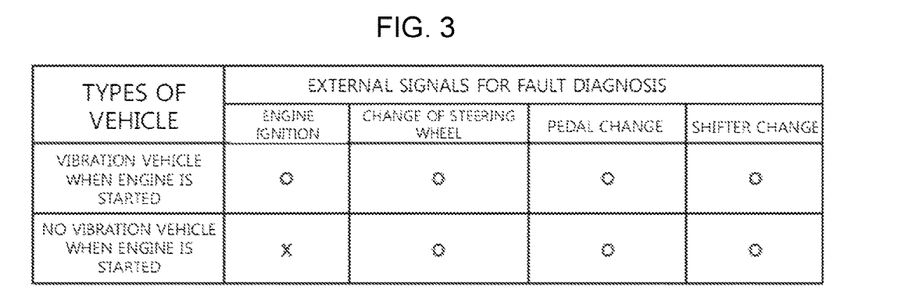
FIG. 3 illustrates external signals for diagnosis of a fault of the bio-signal sensor for vehicles.

FIG. 3 illustrates external signals for diagnosing a fault of the bio-signal sensor for vehicles.

As shown, an external signal which can be used for bio-signal sensor fault diagnosis may be determined depending on vehicle type. When the bio-signal sensor does not have a separate motion detecting function (e.g., motion detecting through a separate sensor including an acceleration, pressure, shock or image sensor), the vehicle including the bio-signal sensor needs to check whether a detected signal varies according to movement of the user or the vehicle and to determine the cause of the Doppler variation to confirm signal transmission and reception states of the bio-signal sensor.

In the case of a vehicle which generates vibration when the engine is started, it is possible to check whether a detected signal varies according to movement of the driver or user or movement of the vehicle on a basis of whether the engine is started, whether the steering wheel is manipulated, whether the pedal is manipulated, whether a shifter is manipulated or the like.

In the case of a vehicle which generates no vibration or weak vibration when the engine is started, it is difficult to check whether a detected signal of the bio-signal sensor varies on the basis of whether the engine is started. Even in this case, however, it is possible to check whether a detected signal varies according to movement of the driver or user or movement of the vehicle on the basis of whether the engine is started, whether the steering wheel is manipulated, whether the pedal is manipulated, whether a shifter is manipulated or the like.

When a signal detected by the bio-signal sensor in response to the external signal for fault diagnosis includes noise, the bio-signal sensor may be determined to normally operate. Conversely, when a signal detected by the bio-signal sensor in response to the external signal for fault diagnosis does not include noise, the bio-signal sensor may be determined to malfunctions.

Figure 4:
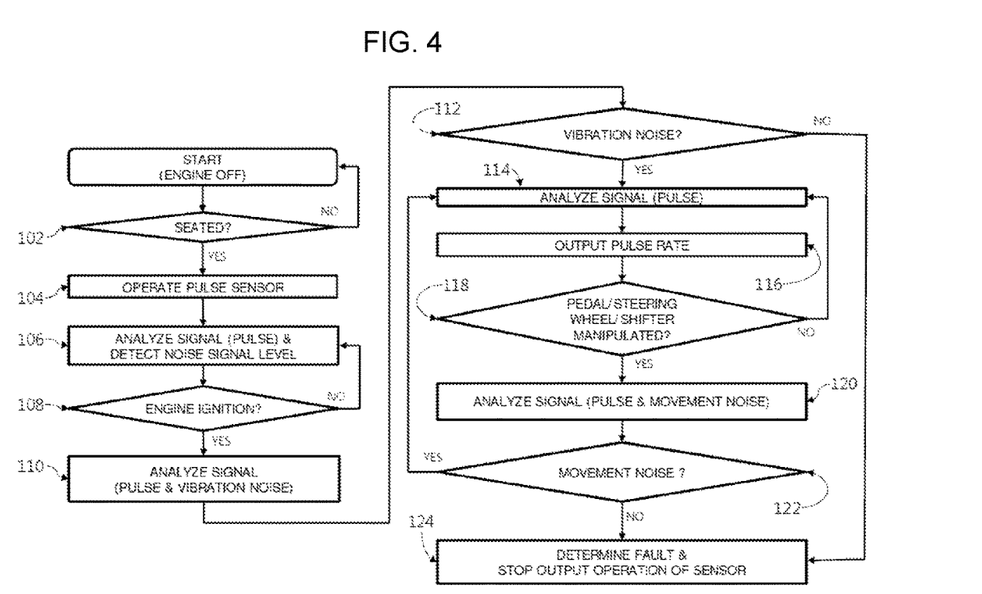
FIG. 4 illustrates a first fault diagnosis method for the bio-signal sensor for vehicles.

FIG. 4 illustrates a first fault diagnosis method for the bio-signal sensor for vehicles.

As shown, the first fault diagnosis method may be applied when a vehicle, which generates vibration when the engine is started, includes a pulse sensor. First of all, whether a user or driver sits on a seat is detected while the engine of the vehicle is turned off 102. When the user or driver sits on the seat, the pulse sensor operates 104. A signal component and a noise component with respect to the pulse of the user or driver are detected from a signal detected by the pulse sensor 106.

Then, whether the engine is started is detected 108. When the engine is started, the signal component and the noise component with respect to the pulse of the user or driver in the detected signal of the pulse sensor are analyzed 110. Here, whether the noise component includes noise caused by vibration due to the engine ignition or the like is checked 112. When the noise component does not include noise caused by vibration due to the engine ignition or the like, the pulse sensor is determined to have malfunctioned and is prevented from outputting a result of the detected signal 124.

If the noise component includes noise caused by vibration due to the engine ignition or the like, the signal component with respect to the pulse of the user or driver in the detected signal of the pulse sensor is analyzed 114 and the analyzed pulse rate is output 116.

Then, the vehicle may sense whether the user or driver manipulates the pedal, steering wheel, shift lever or the like 118. A detected signal of the pulse sensor is analyzed in response to an external input signal corresponding to the manipulation 120. Thereafter, whether the detected signal of the pulse sensor includes noise caused by movement of the user or driver is determined 122. When the detected signal does not include noise, the vehicle may determine that the pulse sensor has malfunctioned 124. When the detected signal includes the noise, a signal component related to the pulse of the user or driver in the detected signal is analyzed 114.

Figure 5:
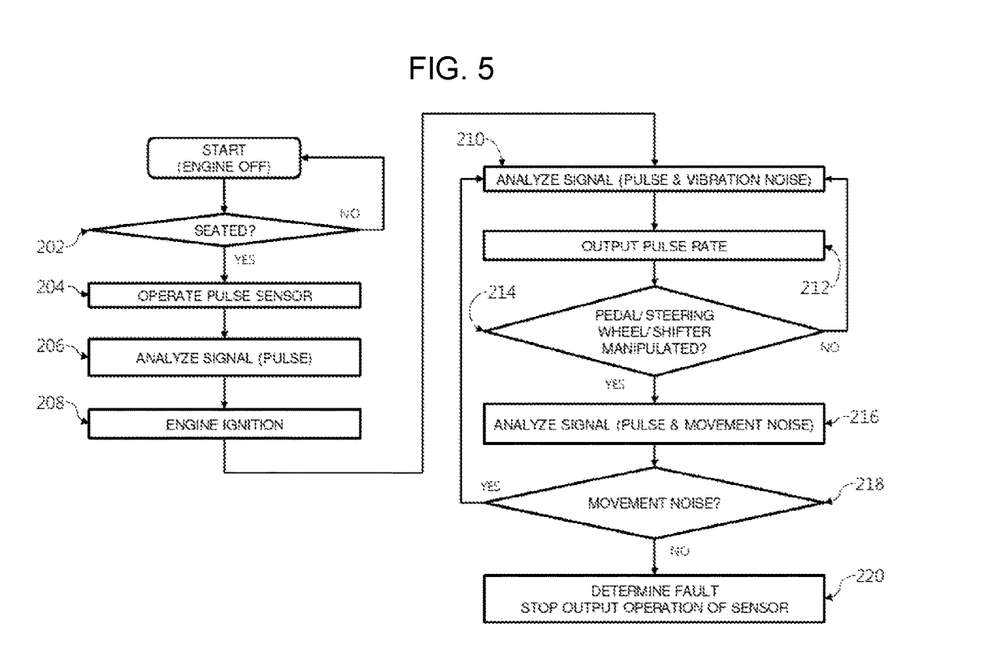
FIG. 5 illustrates a second fault diagnosis method for the bio-signal sensor for vehicles.

FIG. 5 illustrates a second fault diagnosis method for the bio-signal sensor for vehicles.

As shown, the second fault diagnosis method is applicable when a vehicle which generates no vibration or weak vibration when the engine is started includes the pulse sensor. First of all, whether a user or driver sits on a seat is detected while the engine of the vehicle is turned off 202. When the user or driver sits on the seat, the pulse sensor operates 204. A signal component and a noise component with respect to the pulse of the user or driver are detected from a signal detected by the pulse sensor 206.

Then, whether the engine is started is sensed 208. When the engine is started, the signal component and the noise component with respect to the pulse of the user or driver in the sensed signal of the pulse sensor are analyzed 210. However, in the case of the vehicle which generates no vibration or weak vibration when the engine is started, it may not be desirable to determine whether the pulse signal has malfunctioned on the basis of a signal detected by the pulse sensor after the engine is started. The signal component with respect to the pulse of the user or driver in the signal of the pulse sensor is analyzed 210 and the analyzed pulse rate is output 212.

Then, the vehicle may sense whether the user or driver manipulates the pedal, steering wheel, shift lever or the like 214. A sensed signal of the pulse sensor is analyzed in response to an external input signal corresponding to the manipulation 216. Thereafter, whether the detected signal of the pulse sensor includes noise caused by movement of the user or driver is determined 218. When the detected signal does not include noise, the vehicle may determine that the pulse sensor has malfunctioned 220. When the detected signal includes noise, a signal component related to the pulse of the user or driver in the detected signal is analyzed 210.

According to the aforementioned method, it is possible to check whether a detected signal of the pulse sensor varies according to movement of the driver or user and to diagnose a fault of the pulse sensor even in the case of a vehicle which generates no vibration or weak vibration when the engine is started.

Figure 6:
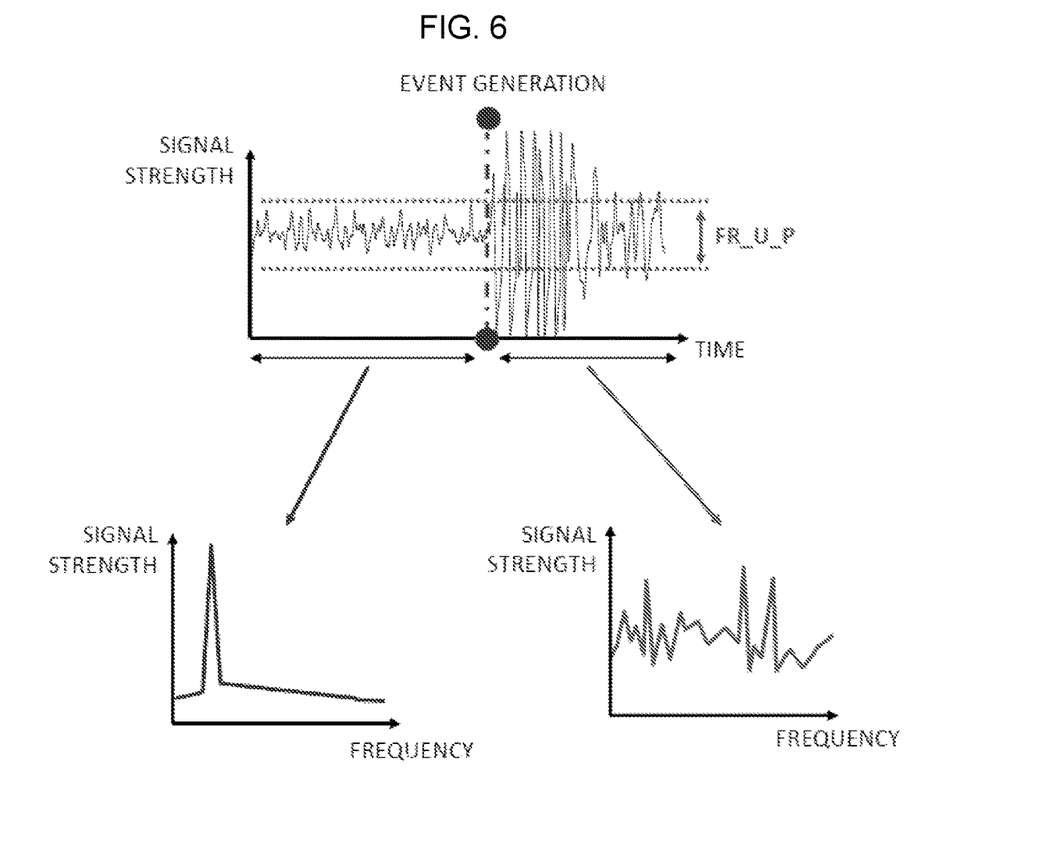
FIG. 6 illustrates a case in which the bio-signal sensor for vehicles normally operates.

FIG. 6 illustrates a case in which the bio-signal sensor for vehicles normally operates.

As shown, variations in signals detected by the bio-signal sensor may be divided into a variation before generation of an event and a variation after generation of the event. Here, the event may include the engine ignition, variation in the steering wheel, variation in the pedal, variation in the shifter or the like.

Variations in signals detected by the bio-signal sensor may be analyzed in the time domain or frequency domain. For example, the received signal strength of a signal sensed by the bio-signal sensor may exceed a range FR_U_P in the time domain due to noise generated after generation of that.

When a signal detected by the bio-signal sensor before generation of the event is analyzed in the frequency domain, the signal may include a signal component corresponding to a bio-signal of the user or driver at a specific frequency. A specific frequency band may be determined as the range in response to the signal component in the frequency domain. When a signal detected by the bio-signal sensor after generation of the event is analyzed in the frequency domain, the signal may include not only a signal component corresponding to a bio-signal of the user or driver but also noise at various frequencies.

Figure 7:
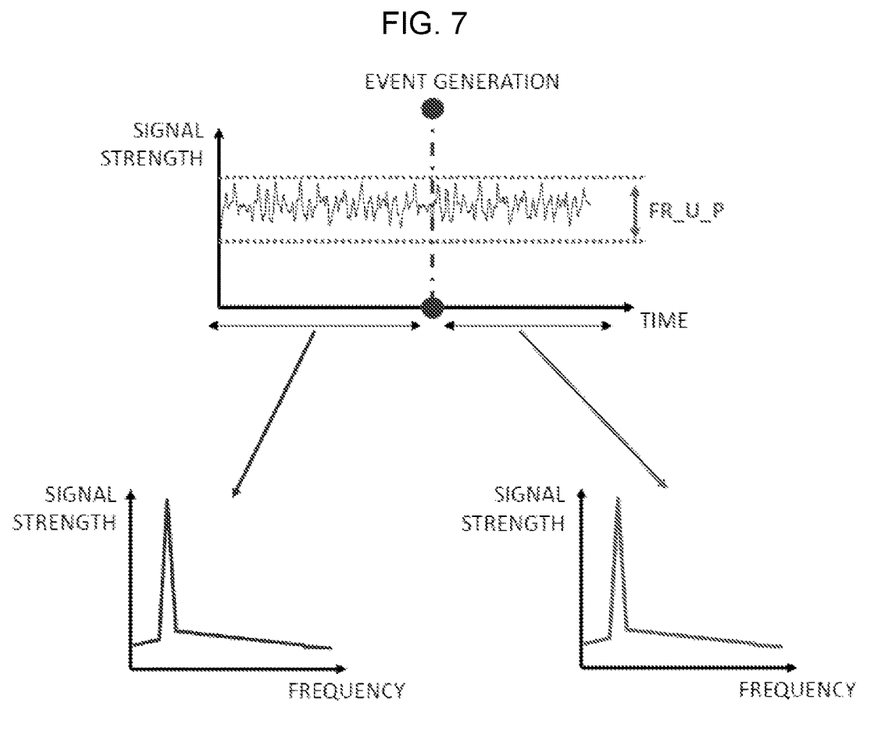
FIG. 7 illustrates a case in which the bio-signal sensor for vehicles does not normally operate.

FIG. 7 illustrates a case in which the bio-signal sensor for vehicles does not normally operate.

As shown, variations in signals detected by the bio-signal sensor may be divided into variation before generation of an event and variation after generation of the event. Here, the event may include the engine ignition, variation in the steering wheel, variation in the pedal, variation in the shifter or the like.

As described above with reference to FIG. 6, variations in signals detected by the bio-signal sensor may be analyzed in the time domain or frequency domain. For example, a range FR_U_P may be set on the basis of a signal detected by the bio-signal sensor before generation of the event in the frequency domain. After generation of the event, a signal detected by the bio-signal sensor is analyzed. Here, when a signal deviated from the range FR_U_P is not generated, the bio-signal sensor may be determined to operate abnormally.

When a signal detected by the bio-signal sensor before generation of the event is analyzed in the frequency domain, the signal may include a signal component corresponding to a bio-signal of the user or driver at a specific frequency. A specific frequency band may be determined as the range in response to the signal component in the frequency domain. When a signal sensed by the bio-signal sensor after generation of the event is analyzed in the frequency domain, the signal may include not only a signal component corresponding to a bio-signal of the user or driver but also noise at various frequencies. However, noise may not be received when the bio-signal sensor does not normally operate. If noise is not received at other frequencies even when an event is generated, the vehicle may determine that the bio-signal sensor does not normally operate.

Figure 8:
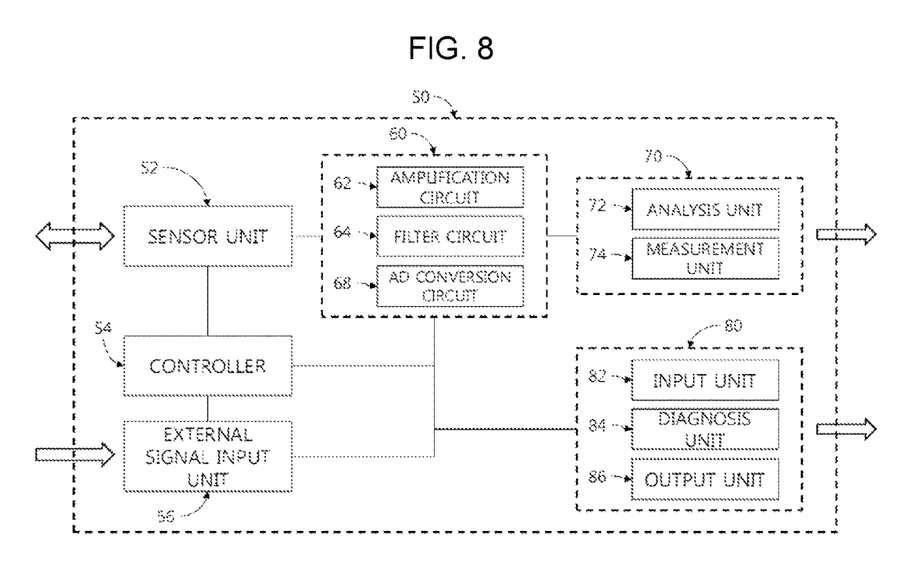
FIG. 8 illustrates an apparatus for diagnosing a fault of the bio-signal sensor for vehicles.

FIG. 8 illustrates an apparatus 50 for diagnosing a fault of a bio-signal sensor for a vehicle.

As shown, the apparatus 50 for diagnosing a fault of the bio-signal sensor may include a receiver 60 for receiving a first bio-signal measured through a sensor 52 including the bio-signal sensor in response to a seating detecting signal and a second bio-signal measured through the sensor 52 in response to input through an on-board interface, and a determination unit 80 for determining whether the bio-signal sensor has a fault according to whether the second bio-signal includes a signal deviating from a range set in response to the first bio-signal.

Furthermore, the receiver 60 may receive a third bio-signal when the engine of the vehicle is started. Upon reception of the third bio-signal, the determination unit 80 may determine whether the bio-signal sensor has a fault according to whether the third bio-signal includes a signal deviating from the range set in response to the first bio-signal.

The receiver 60 may include an amplification circuit 62 for amplifying a received signal, a filter circuit 64 for filtering the received signal through a predetermined frequency band, and an AD conversion circuit 68 for converting the filtered analog signal into a digital signal.

The apparatus 50 for diagnosing a fault of the bio-signal sensor may further include an external signal input device 56 for receiving input through the on-board interface. An external signal input through the external signal input device 56 may be generated by at least one of variation in the steering wheel of the vehicle, variation in the pedal and variation in the shifter. The received external signal may be generated after the engine of the vehicle is started.

In addition, the external signal input device 56 may receive a detected signal with respect to whether the engine is started.

The bio-signal sensor of the sensor 52 may include a pulse sensor. When the bio-signal sensor includes the pulse sensor, the first bio-signal and the second bio-signal may include a pulse detecting signal of a user or a driver. In addition, the pulse sensor may include a noncontact Doppler pulse sensor.

The apparatus 50 for diagnosing a fault of the bio-signal sensor may further include an operation unit 70 for analyzing at least one of the second bio-signal and the third bio-signal and outputting a result within a range. The operation unit 70 may include an analysis unit 72 for analyzing a signal delivered from the receiver 60 and a measurement unit 74 for representing the analyzed signal in a format which can be understood by the user or driver. A value or a signal converted through the measurement unit 74 may be delivered to the user or driver through a display unit provided to the vehicle.

The determination unit 80 may determine whether a signal component included in the signal delivered through the receiver and deviating from the range corresponds to input through the on-board interface or ant delivered through the external signal input device 56, such as the engine ignition. Then, the determination unit 80 may determine whether the bio-signal sensor has malfunctioned in response to the determination result. If the determination unit 80 determines that the signal delivered through the receiver 60 includes a signal component corresponding to the event and deviating from the range, the determination unit 80 may determine that the bio-signal sensor included in the sensor 52 normally operates. Here, the signal delivered to the determination unit 80 through the receiver 60 may include noise according to the input through the on-board interface.

The apparatus 50 for diagnosing a fault of the bio-signal sensor may further include a controller 54 which stops operation of the bio-signal sensor when the determination unit 80 determines that the bio-signal sensor in the sensor 52 has malfunctioned. The controller 54 may control operation of the bio-signal sensor. Specifically, the controller 54 may control the bio-signal sensor to periodically measure a bio-signal and then to output measured bio-signals to the receiver 60.

The aforementioned method according to the embodiment may be implemented as a program executed in a computer and stored in a computer-readable recording medium. Examples of the computer-readable recording medium include a ROM, a RAM, a CD-ROM, a magnetic tape, a floppy disk, an optical data storage device, and a medium using a carrier wave e.g. transmission through the Internet.

The computer-readable recording medium may be distributed to computer systems connected through a network, stored and executed as code readable in a distributed manner. Functional programs, codes and code segments for implementing the aforementioned method may be easily deduced by programmers skilled in the art.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A fault diagnosis method for a bio-signal sensor equipped in a vehicle, comprising:
measuring a first bio-signal through the bio-signal sensor based at least on a seating detecting signal;
measuring a second bio-signal through the bio-signal sensor based at least on an input entered via an on-board interface; and
determining whether the bio-signal sensor has malfunctioned according to whether the second bio-signal includes a signal deviating from a range set in response to the first bio-signal,
wherein the seating detecting signal is detected while an engine of the vehicle is turned off,
wherein the first bio-signal is measured when the seating detecting signal is detected and the engine of the vehicle is turned off, and
wherein the first bio-signal includes a signal component and a noise component with respect to a pulse of a user or driver.

2. The fault diagnosis method according to claim 1, further comprising:
measuring a third bio-signal when the engine of the vehicle is started; and
determining whether the bio-signal sensor has malfunctioned according to whether the third bio-signal includes a signal deviating from the range set in response to the first bio-signal.

3. The fault diagnosis method according to claim 1, wherein the input through the on-board interface includes at least one of variation in a steering wheel, variation in a pedal and variation in a shifter.

4. The fault diagnosis method according to claim 3, wherein the input through the on-board interface is configured to be generated after the engine of the vehicle is started.

5. The fault diagnosis method according to claim 1, wherein the bio-signal sensor includes a pulse sensor, and the first bio-signal and the second bio-signal include pulse-detecting signals.

6. The fault diagnosis method according to claim 5, wherein the pulse sensor is a non-contact Doppler pulse sensor.

7. The fault diagnosis method according to claim 1, wherein the signal deviating from the range includes noise according to the input through the on-board interface.

8. The fault diagnosis method according to claim 1, wherein the determining of whether the bio-signal sensor has malfunctioned comprises:
analyzing at least one of the second bio-signal and the third bio-signal to output a result within the range;
determining whether the signal deviating from the range corresponds to the input through the on-board interface; and
determining whether the bio-signal sensor has malfunctioned in response to a determination result.

9. The fault diagnosis method according to claim 1, further including stopping operation of the bio-signal sensor when the bio-signal sensor is determined to have malfunctioned.

10. An apparatus for performing a fault diagnosis of a bio-signal sensor in a vehicle including a processing system that includes at least one data processor and at least one computer-readable memory storing a computer program, wherein the processing system is configured to cause the apparatus to:
measure a first bio-signal through the bio-signal sensor in response to a seating detecting signal;
measure a second bio-signal through the bio-signal sensor in response to input through an on-board interface; and
determine whether the bio-signal sensor has malfunctioned according to whether the second bio-signal includes a signal deviating from a range set in response to the first bio-signal,
wherein the seating detecting signal is detected while an engine of the vehicle is turned off,
wherein the first bio-signal is measured when the seating detecting signal is detected and the engine of the vehicle is turned off, and wherein the first bio-signal includes a signal component and a noise component with respect to a pulse of a user or driver.

11. The apparatus according to claim 10, wherein the processing system is further configured to cause the apparatus to:
  measure a third bio-signal when the engine of the vehicle is started; and
  determine whether the bio-signal sensor has malfunctioned according to whether the third bio-signal includes a signal deviating from the range set in response to the first bio-signal.

12. A fault diagnosis apparatus for a bio-signal sensor equipped in a vehicle, comprising:
  a receiver for receiving a first bio-signal, measured by the bio-signal sensor based at least on a seating detecting signal, and a second bio-signal measured through the bio-signal sensor based at least on an input entered through an on-board interface; and
  a determination unit for determining whether the bio-signal sensor has malfunctioned according to whether the second bio-signal includes a signal deviating from a range set in response to the first bio-signal,
  wherein the seating detecting signal is detected while an engine of the vehicle is turned off,
  wherein the first bio-signal is measured when the seating detecting signal is detected and the engine of the vehicle is turned off, and
  wherein the first bio-signal includes a signal component and a noise component with respect to a pulse of a user or driver.

13. The fault diagnosis apparatus according to claim 12, wherein the receiver receives a third bio-signal when the engine of the vehicle is started, and the determination unit determines whether the bio-signal sensor has malfunctioned according to whether the third bio-signal includes a signal deviating from the range set in response to the first bio-signal.

14. The fault diagnosis apparatus according to claim 12, further including an external signal input device for receiving input through the on-board interface.

15. The fault diagnosis apparatus according to claim 14, wherein an external signal input to the external signal input device is generated by at least one of variation in a steering wheel, variation in a pedal and variation in a shifter,
  wherein the external signal is generated after the engine of the vehicle is started.

16. The fault diagnosis apparatus according to claim 12, wherein the bio-signal sensor includes a non-contact Doppler pulse sensor, and the first bio-signal and the second bio-signal include pulse-detecting signals.

17. The fault diagnosis apparatus according to claim 12, wherein the signal deviating from the range includes noise according to the input through the on-board interface.

18. The fault diagnosis apparatus according to claim 12, further including an operation unit for analyzing at least one of the second bio-signal and the third bio-signal to output a result within the range.

19. The fault diagnosis apparatus according to claim 12, wherein the determination unit determines whether the signal deviating from the range corresponds to the input through the on-board interface and determines whether the bio-signal sensor has malfunctioned in response to a determination result.

20. The fault diagnosis apparatus according to claim 12, further including a controller configured for stopping operation of the bio-signal sensor when the bio-signal sensor is determined to have malfunctioned,
  wherein the controller is configured to control operation of the bio-signal sensor to cause the bio-signal sensor to with a predetermined time period measure bio-signals and to output measured bio-signals to the receiver.

* * * * *